United States Patent
Yang

(10) Patent No.: US 8,415,944 B1
(45) Date of Patent: Apr. 9, 2013

(54) METHOD FOR STABILIZING AC MAGNETIC SUSCEPTIBILITY OF MAGNETIC FLUID

(75) Inventor: Shieh-Yueh Yang, Taipei (TW)

(73) Assignee: Magqu Co., Ltd., Taipei County (TW)

( * ) Notice: Subject to any disclaimer, the term of this patent is extended or adjusted under 35 U.S.C. 154(b) by 0 days.

(21) Appl. No.: 13/325,508

(22) Filed: Dec. 14, 2011

(51) Int. Cl.
    *G01N 27/74* (2006.01)
(52) U.S. Cl. ..................................... 324/204
(58) Field of Classification Search ............ 324/204
    See application file for complete search history.

(56) References Cited

PUBLICATIONS

Chin-Yih Hong et al., Magnetic susceptibility reduction method for magnetically labeled immunoassay, Applied Physics Letters, 2006, vol. 88.
Chin-Yih Hong et al., Wash-free immunomagnetic detection for serum through magnetic susceptibility reduction, Applied Physics Letters, 2007, vol. 90.
S.Y. Yang et al., Wash-free, antibody-assisted magnetoreduction assays of orchid viruses, Journal of Virological Methods, 2008, pp. 334-337, vol. 149.
S.Y. Yang et al., Independency of Fe ions in hemogoblin on immunomagnetic reduction assay, Journal of Magnetism and Magnetic Materials, 2009, pp. 3266-3269, vol. 321.

*Primary Examiner* — Reena Aurora
(74) *Attorney, Agent, or Firm* — WPAT, P.C.; Anthony King

(57) ABSTRACT

The invention relates to a method for stabilizing ac magnetic susceptibility of a magnetic fluid, comprising the following steps: (A) preparing two reagents of known magnetic concentration, including a first one in a mixture of an $x_{C1}$ μl, $m_1$-emu/g magnetic fluid and a $y_{C1}$ μl PBS solution and a second one in a mixture of an $x_{C2}$ μl, $m_2$-emu/g magnetic fluid and a $y_{C2}$ μl PBS solution, in addition to a to-be-detected reagent in a mixture of an $x_S$ μl, $m_S$-emu/g magnetic fluid and a $y_S$ μl PBS solution: (B) detecting alternatively $\chi_{ac,o}$ signals; (C) calculating a new $\chi_{ac,o}$ value, i.e. $\chi_{ac,cal}$, for S via $$\chi_{ac,cal} = \frac{\chi_{ac,o,S} - \chi_{ac,o,C1}}{\chi_{ac,o,C2} - \chi_{ac,o,C1}} \times (x_{C2} - x_{C1}) + \chi_{C1};$$

and (D) repeating steps (B) and (C) to find the $\chi_{ac,cal}$ for a next run, and then finding a time dependent $\chi_{ac,cal}$ for S.

5 Claims, 7 Drawing Sheets

METHOD FOR STABILIZING AC MAGNETIC SUSCEPTIBILITY OF MAGNETIC FLUID

BACKGROUND OF THE INVENTION

1. Field of the Invention

The present invention relates to a method for stabilizing ac magnetic susceptibility of a magnetic fluid, in particular to a method for reducing the coefficient of variation in the ac magnetic susceptibility for a reagent to a rather low value after calibrating.

2. Description of Related Art

By conjugating bio-probes onto magnetic particles, the magnetic particles are able to label specifically bio-targets. With the association between magnetic particles and bio-targets, the magnetic properties of magnetic particles change. This change acts as a parameter for detecting quantitatively proteins, viruses, bacterial, and chemicals by using bio-functionalized magnetic particles.

In early 2000's, some researchers proposed a method for assaying bio-molecules using magnetic particles. This method is so-called immunomagnetic reduction (IMR) [1]. In IMR, the reagent is a solution having homogeneously dispersed magnetic nanoparticles, which are coated with hydrophilic surfactants (e.g. dextran) and antibodies. Under external multiple ac magnetic fields, magnetic nanoparticles oscillate with the multiple ac magnetic fields via magnetic interaction, as shown in FIG. 1(a), which is an illustration of mechanism for immunomagnetic reduction assay before association between magnetic nanoparticles and biotargets. Thus, the reagent under external multiple ac magnetic fields shows a magnetic property, called mixed-frequency ac magnetic susceptibility $\chi_{ac}$. Hereafter the $\chi_{ac}$ is expressed as $\chi_{ac,o}$ before the association between particles and bio-molecules. Via the antibodies on the outmost shell, magnetic nanoparticles associate with and magnetically label bio-molecules to be detected. Due to the association, magnetic nanoparticles become either larger or clustered, as schematically shown in FIG. 1(b), which is an illustration of mechanism for immunomagnetic reduction assay after the association between magnetic nanoparticles and biotargets. The response of these larger/clustered magnetic nanoparticles to external multiple ac magnetic fields is much less than that of originally individual magnetic nanoparticles. Thus, the $\chi_{ac}$ of the reagent is reduced due to the association between magnetic nanoparticles and detected bio-molecules. Hereafter the $\chi_{ac}$ is expressed as $\chi_{ac,\Phi}$ after the association between particles and bio-molecules. It is obvious that $\chi_{ac,\Phi}$ should be smaller than $\chi_{ac,o}$. This is why the method is referred as ImmunoMagnetic Reduction. In principle, when more to-be-detected bio-molecules are mixed with a reagent, more magnetic nanoparticles become larger/clustered. A larger reduction in $\chi_{ac}$ could be expected for reagents. A quantitative parameter related to the amount of to-be-detected bio-molecules is defined in the following Equation as $$IMR\ signal = (\chi_{ac,o} - \chi_{ac,\Phi})/\chi_{ac,o} \times 100\% \quad (1)$$

According to the description given above, IMR exhibits several unique merits. Firstly, the unbound to-be-detected bio-molecules and magnetic nanoparticles are not necessarily to be removed. They are still in the reagent. So, the assay process of IMR is simple. Secondly, only one kind of antibody is used. Thirdly, IMR is a direct and homogeneous assay, which usually shows high reliability and sensitivity. Fourth, because the amount of reduction in $\chi_{ac}$ can be accurately measured to correspond to the concentration of the to-be-detected bio-molecules, the concentration of the bio-molecules can thus be measured quantitatively.

The diameter of magnetic nanoparticles used for IMR is tens of nanometers. The magnetic material of the nanoparticles could be ferrite, e.g. $Fe_3O_4$. The magnetic nanoparticles are well and homogeneously suspended in a water-based solution. The particle concentration of the magnetic reagent is about $10^{12}$ particles/$cm^3$. The distance between two neighboring magnetic nanoparticles is around the order of magnitude of micrometers. Hence, the magnetic interaction between two neighboring magnetic particles is very weak, almost negligible. Therefore, the magnetic particles dispersed in reagent can be regarded as independent particles. But magnetic particles in reagent do experience several kinds of interactions, such as gratify, buoyancy, and thermal motion. The interactions of gravity and buoyancy cancel with each other. The magnetic particles in reagent only experience the thermal motion. Thermal energy $U_{Th}$, for a magnetic particle in reagent can be expressed as $$U_{Th} = k_B T, \quad (2)$$

where $k_B$ is a Boltzmann constant ($=1.38\times10^{-23}$ $m^2$-kg-$s^{-2}$-$K^{-1}$), and T is the temperature in unit of Kelvin K. For example, at 25° C. (=298 K), the thermal energy $U_{Th}$ is $4.11\times10^{-21}$ J for a magnetic particle in regent via Eq. (1).

As a magnetic field B applied to the magnetic reagent, a magnetic energy $U_m$ is generated for the magnetic particle in reagent. The $U_m$ can be expressed as $$U_m = -mB, \quad (3)$$

where m is a magnetic moment of a magnetic particle. The m can be obtained via $$m = vM, \quad (4)$$

where v is the volume of a magnetic particle, and M is magnetization of the magnetic material forming the particle. For a magnetic particle of 93 nm in diameter, the volume v is $(4/3)\pi(93/2)^3$ $nm^3$. If the magnetic material is ferrite, e.g. $Fe_3O_4$, the M is $4.75\times10^{-4}$ A-$nm^{-1}$. Therefore, the m becomes 200 A-$nm^2$.

In IMR, the amplitude of the applied ac magnetic field is in an order of magnitude of several Gauss's, say 1 Gauss. Thus, the absolute value of $U_m$ is found as $2.00\times10^{-20}$ J via Eq. (3). The $U_m$ is just five times as $U_{Th}$. This implies that the thermal energy plays a role in detecting the ac magnetic susceptibility $\chi_{ac}$ of reagent in IMR. Theoretically, as the temperature rises, the thermal energy is enhanced to depress the magnetic actions of magnetic particles under ac magnetic fields. As a result, the $\chi_{ac}$ of magnetic reagent is reduced as the temperature becomes higher. However, once the temperature is reduced, the magnetic actions become more dominant. Thus, the $\chi_{ac}$ of magnetic reagent goes up at a lower temperature. It is worthy noting that such changes in $\chi_{ac}$ of reagent are due to the variation in temperature, not due to the association between the magnetic particles and bio-targets. This means that the un-stability in temperature easily leads to false reduction or increase in the ac magnetic susceptibility $\chi_{ac}$ of reagent in IMR.

In addition to thermal interaction, there are several factors causing the un-stability for ac magnetic susceptibility of magnetic reagent. These factors include background noise of an analyzer, un-stability of electronic circuits to amplify the detected ac magnetic susceptibility of reagent, etc. Methods to improve these bad issues for IMR are needed to be developed.

One possible method to stabilize the temperature is to use a temperature controller. There have been lots of commercial modules for controlling temperature. However, other control modules are needed to well control the fluctuation in the background noise of the analyzer and the performance of the amplifying circuits. In such a case, the analyzer able to obtain stable signals for ac magnetic susceptibility of reagent would be very complicated, and also costs a lot.

In a known proposed approach, the magnetic reagent used is the dextran-coated $Fe_3O_4$ magnetic particles dispersed in a PBS solution. The mean value and the standard deviation for particle diameter are respectively 93.6 nm and 23.8 nm, as shown in FIG. 2, which illustrates distribution for the diameter of dextran-coated $Fe_3O_4$ particles. The saturated magnetization of the reagent is 0.1 emu/g.

The reagent is put into the analyzer for detecting the time-dependent ac magnetic susceptibility $\chi_{ac,o}$. Meanwhile, the time dependent temperature is recorded. The results are shown in FIGS. 3(a) and 3(b), which respectively illustrate time dependent (a) temperature around reagent and (b) detected $\chi_{ac,o}$. During the detection, the temperature varies with time, as shown in FIG. 3(a). The highest temperature is 25.9° C., and the lowest temperature is 22.6° C. The detected time dependent $\chi_{ac,o}$ is shown in FIG. 3(b). It can be found that the $\chi_{ac,o}$ varies significantly with time. The variation in $\chi_{ac,o}$ is due to not only the temperature fluctuation, but also the noise of the analyzer and the amplifying gain of the electronics. According to the data shown in FIG. 3(b), the maximum and the minimum values for $\chi_{ac,o}$ are 142.1 and 124.3, respectively. The mean value and the standard deviation for the detected $\chi_{ac,o}$'s are 118.0 and 10.68, respectively. Thus, the coefficient of variation for the time dependent $\chi_{ac,o}$ is 9.05%. This means that the noise level for IMR is 9.05%. However, according to the reported papers [Attachments 2-4], the IMR signals are within the range from 0.80% to 3.00% by well controlling the temperature of reagent, background noise of the analyzer, and gain of amplifying circuits. The value of 9.05% for the variation in $\chi_{ac,o}$ found in FIG. 3(b) is much higher than the true IMR signals. It fails to detect the IMR signals if the variation in $\chi_{ac,o}$ could not be reduced.

As far as the related prior art is concerned, references may be referred to the following:

[1] Chin-Yih Hong, C. C. Wu, Y. C. Chiu, S. Y. Yang, H. E. Horng, and H. C. Yang, "*Magnetic susceptibility reduction method for magnetically labeled immunoassay*", Appl. Phys. Lett., 88, 212512 (2006).

[2] Chin-Yih Hong, W. H. Chen, Z. F. Jian, S. Y. Yang, H. E. Horng, L. C. Yang, and H. C. Yang, "*Wash-free immunomagnetic detection for serum through magnetic susceptibility reduction*", Appl. Phys. Lett., 90, 74105 (2007).

[3] S. Y. Yang, Z. F. Jian, J. J. Chieh, H. E. Horng, H. C. Yang, and Chin-Yih Hong, "*Wash-free, antibody-assisted magnetoreduction assays on orchid viruses*", J. Virol. Methods, 149, 334 (2008).

[4] S. Y. Yang, C. B. Lan, C. H. Chen, H. E. Horng, Chin-Yih Hong, H. C. Yang, Y .K. Lai, Y. H. Lin, and K. S. Teng, "*Independency of Fe ions in hemoglobin on immunomagnetic reduction assay*", J. Magn. Magn. Mater. 321, 3266 (2009).

Therefore, it is desirable to provide an improved method to stabilize the ac magnetic susceptibility of magnet reagent without using control modules so as to overcome the aforementioned problems.

SUMMARY OF THE INVENTION

The objective of the present invention is to provide an effective method to stabilize the ac magnetic susceptibility of magnet reagent and thus to reduce the variation in $\chi_{ac,o}$ of the magnetic reagent.

To achieve the objective, the method of the present invention includes the following steps:

(A) preparing two reagents of known magnetic concentration, including a first one in a mixture of an $x_{C1}$ µl (micro liter), $m_1$-emu/ml magnetic fluid and a $y_{C1}$ µl PBS (Phosphate Buffer Saline) solution and a second one in a mixture of an $x_{C2}$ µl, $m_2$-emu/ml magnetic fluid and a $y_{C2}$ µl PBS solution, in addition to a to-be-detected reagent in a mixture of an $x_S$ µl, $m_S$-emu/ml magnetic fluid and a $y_S$ µl PBS solution, in which the two reagents of known magnetic concentration are respectively referred to as C1 and C2, and the to-be-detected reagent is referred to as S, while meeting with the following requirements:

$$m_1 x_{C1} > m_s x_S > m_2 x_{C2};$$

(B) detecting alternatively $\chi_{ac,o}$ signals, denoting mixed-frequency ac magnetic susceptibility $\chi_{ac}$ before association between magnetic nanoparticles and bio-particles, of each of background (without any reagent) and the above-said three reagents in a predetermined sequence of time intervals so as to obtain average values of detected $\chi_{ac,o}$ signals during each interval, which are referred to as $\chi_{ac,o,B}$, $\chi_{ac,o,C1}$, $\chi_{ac,o,S}$, $\chi_{ac,o,C2}$ for background, C1, S, and C2, respectively;

(C) calculating a new $\chi_{ac,o}$ value, i.e. $\chi_{ac,cal}$, for S, a to-be-detected reagent via $$\chi_{ac,cal} = \frac{\chi_{ac,o,S} - \chi_{ac,o,C1}}{\chi_{ac,o,C2} - \chi_{ac,o,C1}} \times \frac{m_2 x_{C2} - m_1 x_{C1}}{m_s} + \frac{m_1}{m_s} x_{C1}; \text{ and}$$

(D) repeating steps (B) and (C) to find the $\chi_{ac,cal}$ for a next run, and then finding a time dependent $\chi_{ac,cal}$ for S.

With the provision of the time dependent $\chi_{ac,cal}$ for S, capable of reducing the coefficient of variation in the ac magetic susceptibility for the reagent to an amount of 0.17% after calibrating the original $\chi_{ac,o}$ to $\chi_{ac,cal}$, the method of the invention is able to stabilize the ac magnetic susceptibility of magnet reagent without using control modules.

Other objectives, advantages, and novel features of the invention will become more apparent from the following detailed description when taken in conjunction with the accompanying drawings.

DETAILED DESCRIPTION OF THE PREFERRED EMBODIMENT

A method to reduce the variation in $\chi_{ac,o}$ of reagent according to the invention comprises the following steps.

1. Preparing two reagents of known magnetic concentration:

For a preferred embodiment, a first one is a mixture of an $x_{C1}$ μl, $m_S$-emu/ml magnetic fluid and a $y_{C1}$ μl PBS (Phosphate Buffer Saline) solution. A second one is a mixture of an $x_{C2}$ μl, $m_S$-emu/ml magnetic fluid and a $y_{C2}$ μl PBS solution. These two reagents are referred to as C1 and C2, respectively. Notably, a to-be-detected reagent is a mixture of an $x_S$ μl, $m_S$-emu/ml magnetic fluid and a $y_S$ μl PBS solution. The to-be-detected reagent is referred to as S. It is suggested to follow these requirements:

$$m_1 x_{C1} > m_S x_S > m_2 x_{C2} \qquad (5)$$

In a preferred embodiment, $x_{C1}=42$, $y_{C1}=58$, $x_{C2}=38$, $y_{C2}=62$, $x_S=40$, $y_S=60$, and $m_1=m_2=m_s=0.1$.

Figure 4:
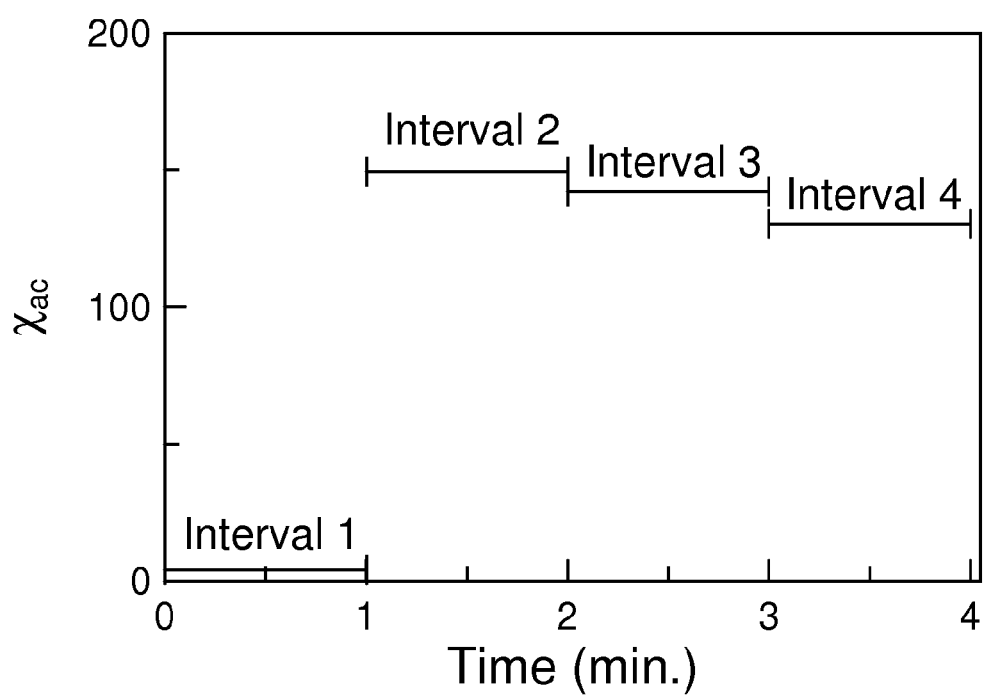
FIG. 4 shows sequence for detecting the ac magnetic susceptibility of background and reagents according to the invention.

2. Detecting alternatively the $\chi_{ac,o}$ signals of background and these three reagents:

As illustrated in FIG. 4, showing sequence for detecting the ac magnetic susceptibility of background and reagents according to the invention, for the time interval from 0 to 1 minute (Interval 1), the $\chi_{ac,o}$ signal of the background (without any reagent) is detected. From the time interval from 1 to 2 minutes (Interval 2), the the $\chi_{ac,o}$ signal of C1 is detected. From the time interval from 2 to 3 minutes (Interval 3), the the $\chi_{ac,o}$ signal of S is detected. From the time interval from 3 to 4 minutes (Interval 4), the the $\chi_{ac,o}$ signal of C2 is detected. The average values of detected $\chi_{ac,o}$ signals during each interval are referred as $\chi_{ac,o,C1}$, $\chi_{ac,o,S}$, $\chi_{ac,o,C2}$ for C1, S, and C2, respectively.

3. Calculating the new $\chi_{ac,o}$ value for S via $$\chi_{ac,cal} = \frac{\chi_{ac,o,S} - \chi_{ac,o,C1}}{\chi_{ac,o,C2} - \chi_{ac,o,C1}} \times \frac{m_2 x_{C2} - m_1 x_{C1}}{m_s} + \frac{m_1}{m_s} x_{C1}. \qquad (6)$$

Figure 1A:
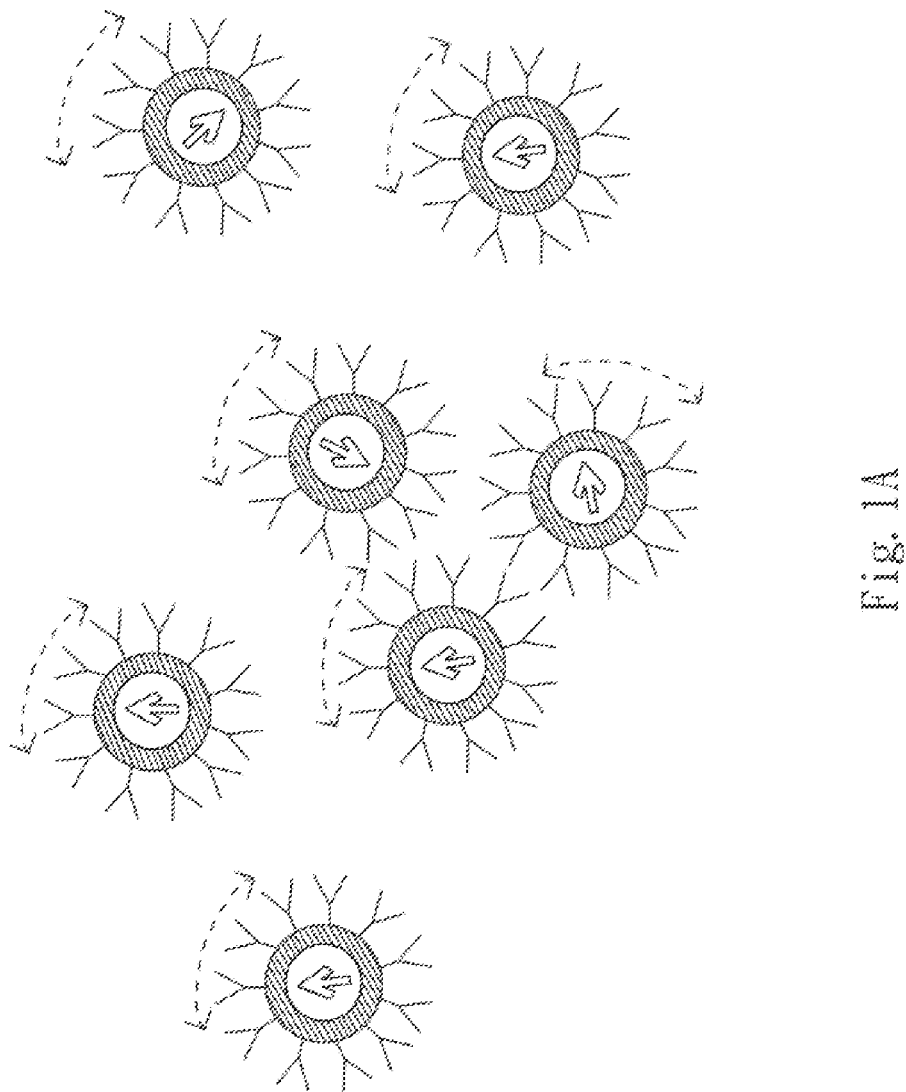
FIG. 1 is an illustration of mechanism for immunomagnetic reduction assay (a) before and (b) after the association between magnetic nanoparticles and biotargets.
Figure 1B:
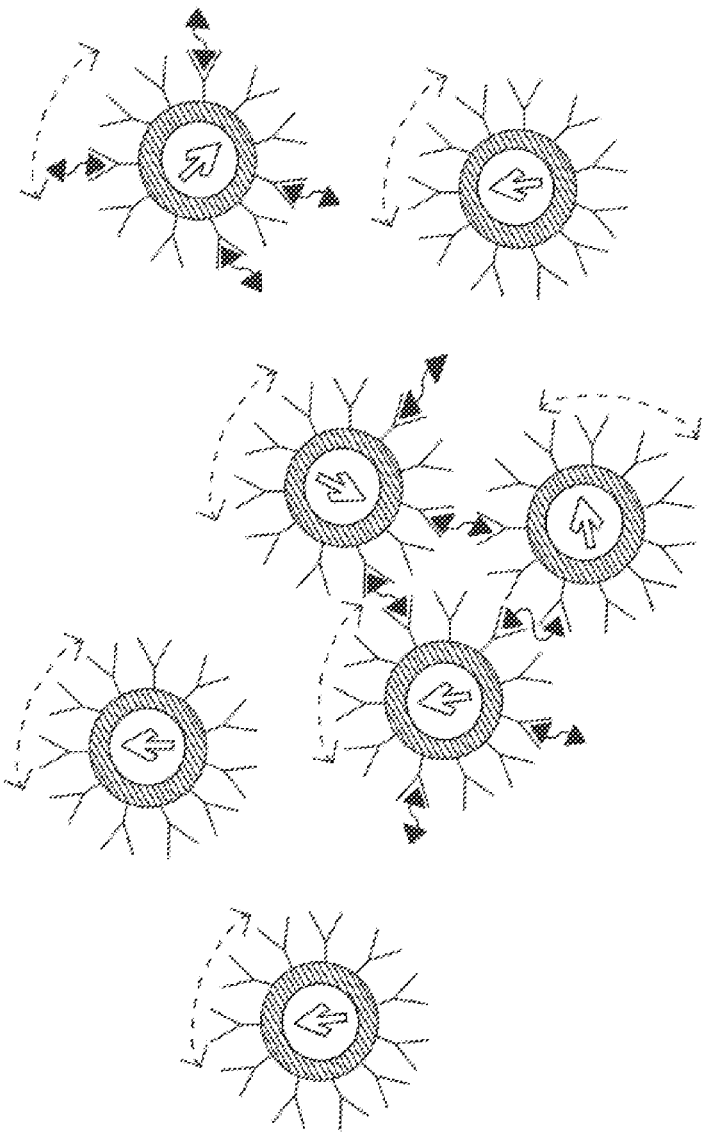
Figure 2:
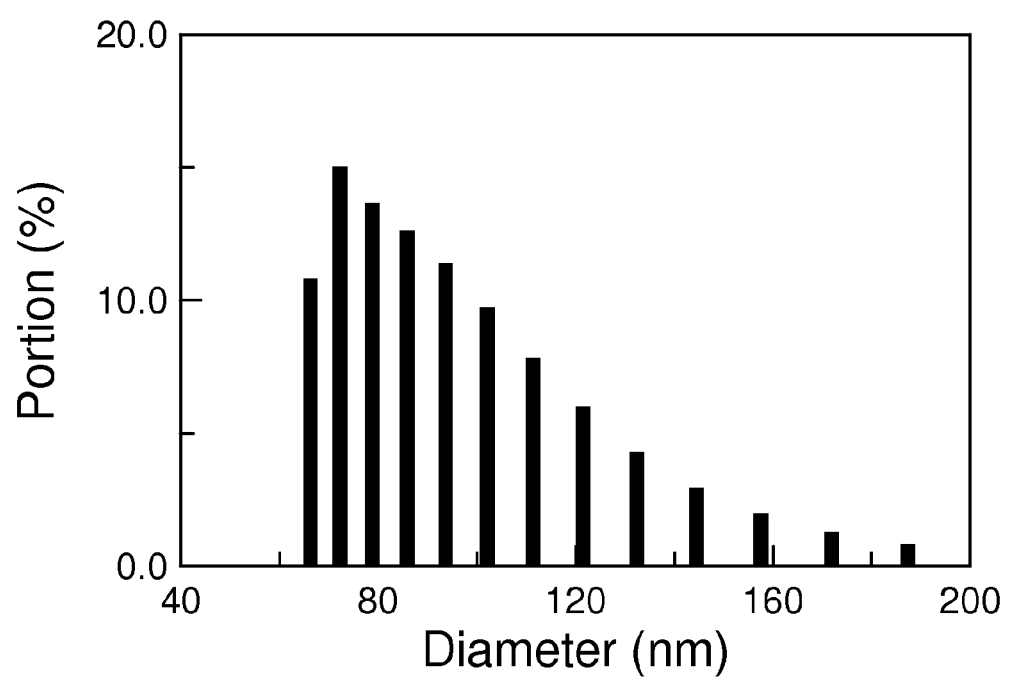
FIG. 2 shows distribution for the diameter of dextran-coated $Fe_3O_4$ particles.
Figure 3:
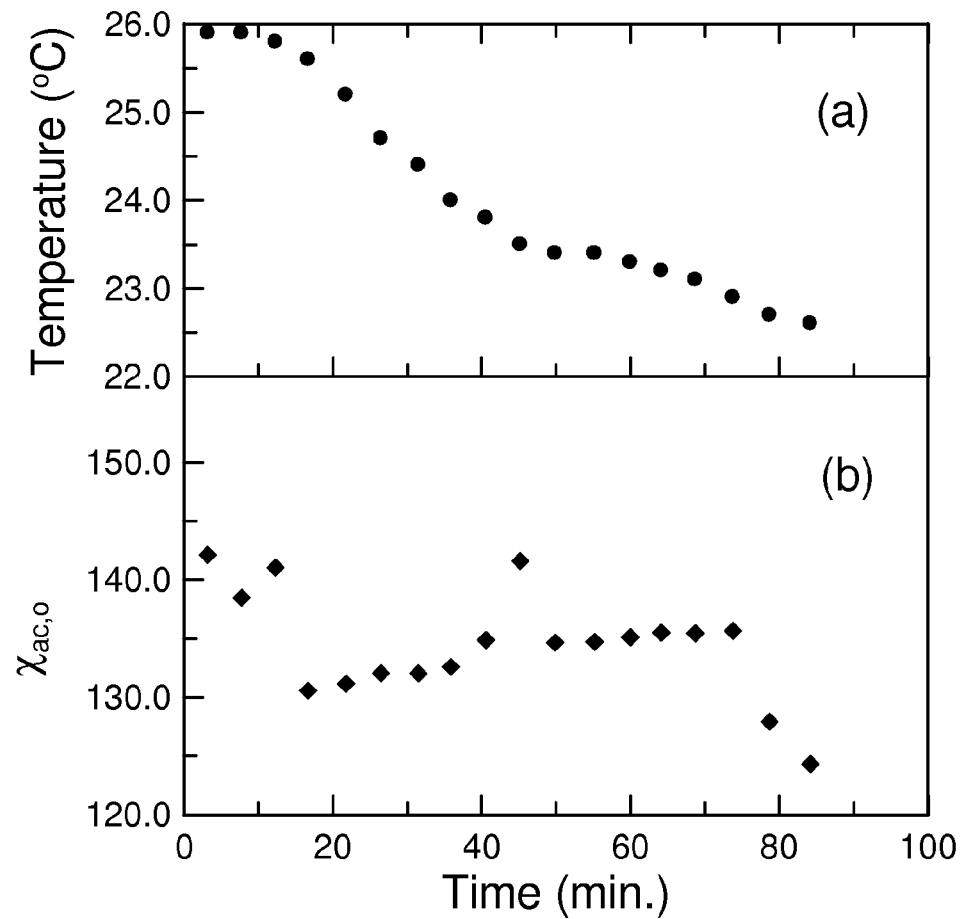
FIG. 3 illustrates time dependent (a) temperature around reagent (b) detected $\chi_{ac,o}$.
Figure 5:
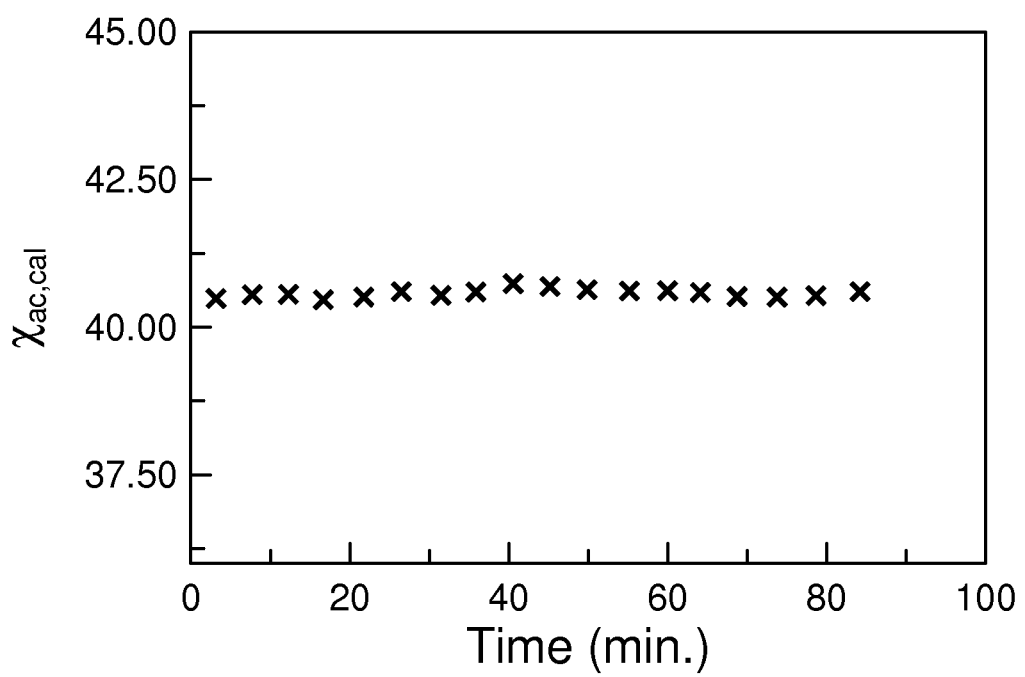
FIG. 5 shows time dependent $\chi_{ac,cal}$ after calibrating $\chi_{ac,o}$ to $\chi_{ac,cal}$ via Eq. (7) according to the invention.

4. Repeating steps 2-3 to find the $\chi_{ac,cal}$ for the next run, and then finding the time dependent $\chi_{ac,cal}$ for S:

The results for the time dependent $\chi_{ac,cal}$ for S are plotted in FIG. 5, showing time dependent $\chi_{ac,cal}$ after calibrating $\chi_{ac,o}$ to $\chi_{ac,cal}$ via Eq. (6) according to the invention. It is worthy noting that the original $\chi_{ac,o}$ are the data shown in FIG. 3(b). The maximum and the minimum values for $\chi_{ac,cal}$ in FIG. 5 are 40.73 and 40.46, respectively. The mean value and the standard deviation for the time dependent $\chi_{ac,cal}$ are 40.57 and 0.07, respectively. This results in a value of 0.17% for the coefficient of variation in $\chi_{ac,cal}$. As compared with the results shown in FIG. 3(b) and FIG. 5, the coefficient of variation in the ac magnetic susceptibility for reagent is reduced from 9.05% to 0.17% after calibrating the original $\chi_{ac,o}$ to $\chi_{ac,cal}$. As such, the variation in the ac magnetic susceptibility of reagent in the instant invention is much lower than the lowest level for the IMR signal (=0.80%).

Figure 6:
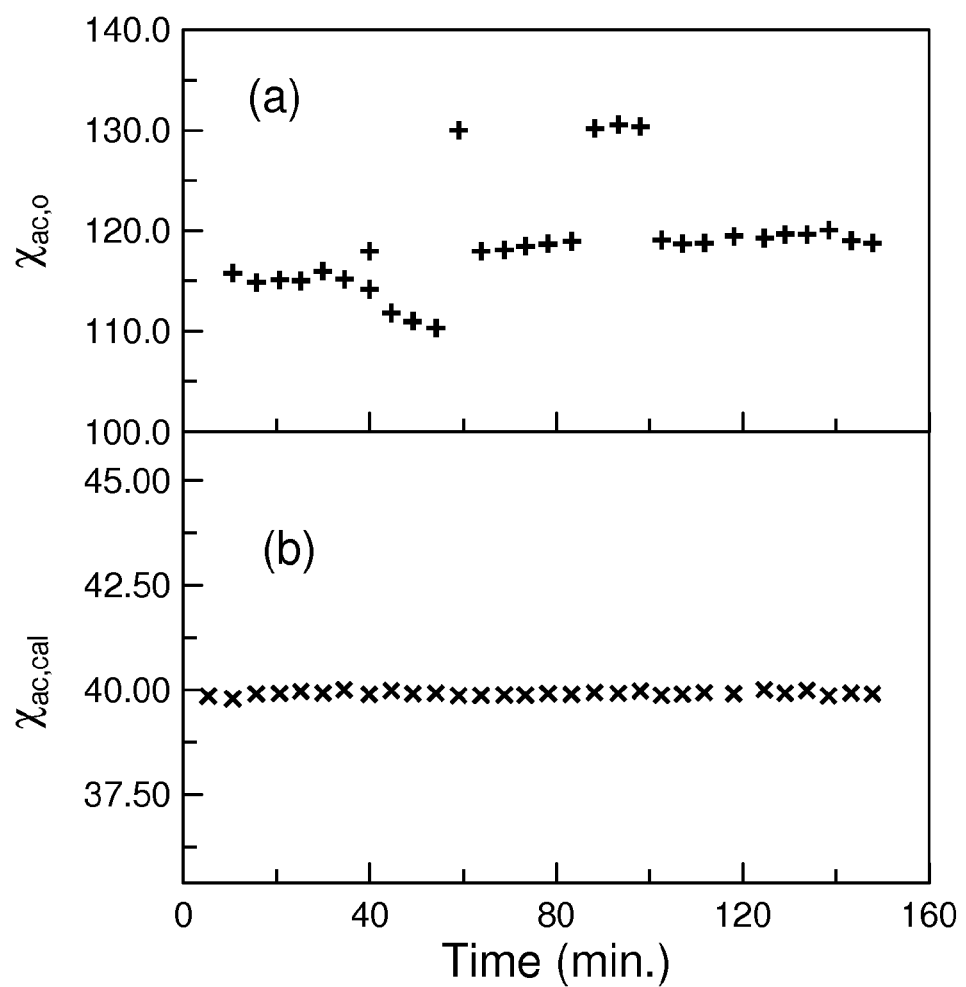
FIG. 6 shows time-dependent (a) detected ac magnetic susceptibility $\chi_{ac,o}$ and (b) calibrated ac magnetic susceptibility $\chi_{ac,cal}$ of the to-be-detected reagent.

In a further preferred embodiment, $m_1=m_2=m_s=0.1$, $x_{C1}=44$, $y_{C1}=56$, $x_{C2}=36$, $y_{C2}=64$, $x_S=40$, and $y_S=60$. These reagents are put into the analyzer for detecting the time-dependent ac magnetic susceptibility $\chi_{ac,o}$ for the to-be-detected reagent. The detected time dependent $\chi_{ac,o}$ is shown in FIG. 6(a). It can be found that the $\chi_{ac,o}$ varies significantly with time. According to the data shown in FIG. 6(a), the maximum and the minimum values for $\chi_{ac,o}$ are 130.6 and 110.4, respectively. The mean value and the standard deviation for the detected $\chi_{ac,o}$'s are 118.8 and 5.28. Thus, the coefficient of variation for the time dependent $\chi_{ac,o}$ is 4.44%. This means that the noise level for IMR is 4.44%.

By using the method to reduce the variation in $\chi_{ac,o}$ of to-be-detected reagent developed in this work, the results for the time dependent $\chi_{ac,cal}$ for the to-be-detected reagent S are plotted in FIG. 6(b). The maximum and the minimum values for $\chi_{ac,cal}$ in FIG. 6(b) are 40.00 and 39.79, respectively. The mean value and the standard deviation for the time dependent $\chi_{ac,cal}$ are 39.91 and 0.05. This results in a value of 0.13% for the coefficient of variation in $\chi_{ac,cal}$. As compare the results shown in FIG. 6(b) and FIG. 6(a), the coefficient of variation in the ac magnetic susceptibility for the to-be-detected reagent is reduced from 4.44% to 0.13% after calibrating the original $\chi_{ac,o}$ to $\chi_{ac,cal}$.

Although the present invention has been explained in relation to its preferred embodiment, it is to be understood that any other possible modifications and variations can be made without departing from the scope of the invention as hereinafter claimed.

I claim:

1. A method for stabilizing ac magnetic susceptibility of a magnetic fluid, comprising the following steps:

(A) preparing two reagents of known magnetic concentration, including a first one in a mixture of an $x_{C1}$ micro liter, $m_1$-emu/ml magnetic fluid and a $y_{C1}$ micro liter Phosphate Buffer Saline solution and a second one in a mixture of an $x_{C2}$ micro liter, $m_2$-emu/ml magnetic fluid and a $y_{C2}$ micro liter Phosphate Buffer Saline solution, in addition to a to-be-detected reagent in a mixture of an $x_S$ micro liter, $m_S$-emu/ml magnetic fluid and a $y_S$ micro liter Phosphate Buffer Saline solution, in which the two reagents of known magnetic concentration are respectively referred to as C1 and C2, and the to-be-detected reagent is referred to as S, while meeting with the following requirements:

$$m_1 x_{C1} > m_S x_S > m_2 x_{C2};$$

(B) detecting alternatively $\chi_{ac,o}$ signals, denoting mixed-frequency ac magnetic susceptibility $\chi_{ac}$ before association between magnetic nanoparticles and bio-particles, of each of background, being without any reagent, and the above-said three reagents in a predetermined sequence of time intervals so as to obtain average values of detected $\chi_{ac,o}$ signals during each interval, which are referred to as $\chi_{ac,o,B}$, $\chi_{ac,o,C1}$, $\chi_{ac,o,S}$, $\chi_{ac,o,C2}$ for background, C1, S, and C2, respectively;

(C) calculating a new $\chi_{ac,o}$ value, i.e. $\chi_{ac,cal}$, for S, a to-be-detected reagent via $$\chi_{ac,cal} = \frac{\chi_{ac,o,S} - \chi_{ac,o,C1}}{\chi_{ac,o,C2} - \chi_{ac,o,C1}} \times \frac{m_2 x_{C2} - m_1 x_{C1}}{m_s} + \frac{m_1}{m_s} x_{C1}; \text{ and}$$

(D) repeating steps (B) and (C) to find the $\chi_{ac,cal}$ for a next run, and then finding a time dependent $\chi_{ac,cal}$ for S.

2. The method for stabilizing ac magnetic susceptibility of a magnetic fluid as claimed in claim 1, wherein $x_{C1}=44$, $y_{C1}=56$, $x_{C2}=36$, $y_{C2}=64$, $x_S=40$, $y_S=60$ and $m_s=0.1$.

3. The method for stabilizing ac magnetic susceptibility of a magnetic fluid as claimed in claim 1, wherein $x_{C1}=42$, $y_{C1}=58$, $x_{C2}=38$, $y_{C2}=62$, $x_S=40$, $y_S=60$ and $m_s=0.1$.

4. The method for stabilizing ac magnetic susceptibility of a magnetic fluid as claimed in claim 1, wherein at the predetermined sequence of time intervals, in a first time interval from 0 to 1 minute (Interval 1), the $\chi_{ac,o}$ signal of the background, being without any reagent, is detected, from a second time interval from 1 to 2 minutes, the $\chi_{ac,o}$ signal of C1 is detected, from a time interval from 2 to 3 minutes, the $\chi_{ac,o}$ signal of S is detected, and from a time interval from 3 to 4 minutes, the $\chi_{ac,o}$ signal of C2 is detected.

5. The method for stabilizing ac magnetic susceptibility of a magnetic fluid as claimed in claim 1, wherein a maximum and a minimum values for the time dependent $\chi_{ac,cal}$ for S are 40.73 and 40.46, respectively and a mean value and a standard deviation for the time dependent $\chi_{ac,cal}$ are 40.57 and 0.07, respectively, resulting in a value of 0.17% for a coefficient of variation in $\chi_{ac,cal}$.

* * * * *